United States Patent [19]

Bauer et al.

[11] 4,030,834
[45] June 21, 1977

[54] DYNAMIC MULTISTATION PHOTOMETER

[75] Inventors: Martin L. Bauer, Oak Ridge; Wayne F. Johnson, Loudon; Dale G. Lakomy, Knoxville, all of Tenn.

[73] Assignee: The United States of America as represented by the United States Energy Research and Development Administration, Washington, D.C.

[22] Filed: Apr. 8, 1976

[21] Appl. No.: 675,085

[52] U.S. Cl. .................. 356/197; 23/259; 233/11; 233/26
[51] Int. Cl.² ............ G01N 21/24; B04B 9/02
[58] Field of Search ............ 356/197; 23/259; 233/11, 26

[56] References Cited
UNITED STATES PATENTS 3,777,172  12/1973  Clarke ..................... 356/197
3,801,004  4/1974  Martin ..................... 356/197

Primary Examiner—Vincent P. McGraw
Attorney, Agent, or Firm—Dean E. Carlson; Stephen D. Hamel; Louis M. Deckelman

[57] ABSTRACT

A portable fast analyzer is provided that uses a magnetic clutch/brake to rapidly accelerate the analyzer rotor, and employs a microprocessor for automatic analyzer operation. The rotor is held stationary while the drive motor is run up to speed. When it is desired to mix the sample(s) and reagent(s), the brake is deenergized and the clutch is energized wherein the rotor is very rapidly accelerated to the running speed. The parallel path rotor that is used allows the samples and reagents to be mixed the moment they are spun out into the rotor cuvetes and data acquisition begins immediately. The analyzer will thus have special utility for fast reactions.

4 Claims, 2 Drawing Figures

DYNAMIC MULTISTATION PHOTOMETER

This invention was made in the course of, or under, a contract with the United States Energy Research and Development Administration.

BACKGROUND OF THE INVENTION

In order to improve the Miniature Fast Photometer Analyzer of U.S. Pat. No. 3,798,459 to N. G. Anderson, et al., issued Mar. 19, 1974, it was desired to accomplish the mixing in the rotor cuvetes and initiate the data acquisition in substantially less than the six seconds normally taken in the fast analyzer. It was found that with the use of a seventeen cuvete mixing rotor such as disclosed in U.S. Pat. No. 3,744,974, to W. L. Maddox et al., issued Nov. 30, 1971, in the above Anderson, et al. patent, which rotor has parallel channels for directing the respective samples and reagents into the respective rotor cuvetes, the simple act of accelerating the rotor was sufficient to adequately mix the sample and reagent to perform the respective chemical reactions. The Miniature Fast Analyzer, however, did not have sufficient accelerating power and, as a consequence, the reactions could not be monitored until after significant time delay which was, in some cases, undesirable. Thus, there exists a need for providing some means for effecting the fast mixing of the respective samples and reagents in the analyzer rotor cuvetes such that the rapid monitoring of the resultant chemical reactions in the rotor cuvetes could be effected. The present invention was conceived to meet this need in a manner to be described hereinbelow.

SUMMARY OF THE INVENTION

It is the primary object of the present invention to provide a small, portable fast photometer analyzer capable of monitoring chemical reactions that start in the first 100 msec after the respective samples and reagents are mixed in the analyzer rotor cuvetes, and which may be completely reacted in the next 100 msec.

It is another object of the present invention to provide a small photometer analyzer for monitoring very fast reactions wherein the respective samples and reagents are rapidly mixed in the centrifugal field of a rotating analyzer rotor thus effecting the rapid clearing away of any bubbles or froth from the reactions that would interfere with data taking.

The above objects have been accomplished in the present invention by providing a clutch/brake mechanism that allows the motor for driving the analyzer rotor to be running at full speed (about 4500 rpm) with the rotor held stationary. When the brake is deenergized and the clutch is energized, the rotor is rapidly accelerated in less than 100 msec to the running speed of 4000 rpm. The solutions will have been mixed in the rotor cuvetes by this acceleration and the analyzer will immediately begin monitoring the transmission, fluorescence, light scattering, or chemiluminescence of the reaction mixtures.

Further, a microprocessor is utilized that performs both the operating and monitoring functions of the analyzer. These include setting the motor speed and the high voltage of the photomultiplier tube, controlling the selection of the proper filter corresponding to the type of reaction being performed, and reducing the data from the chemical reactions to concentration or activity units.

DESCRIPTION OF THE PREFERRED EMBODIMENT

Figure 1:
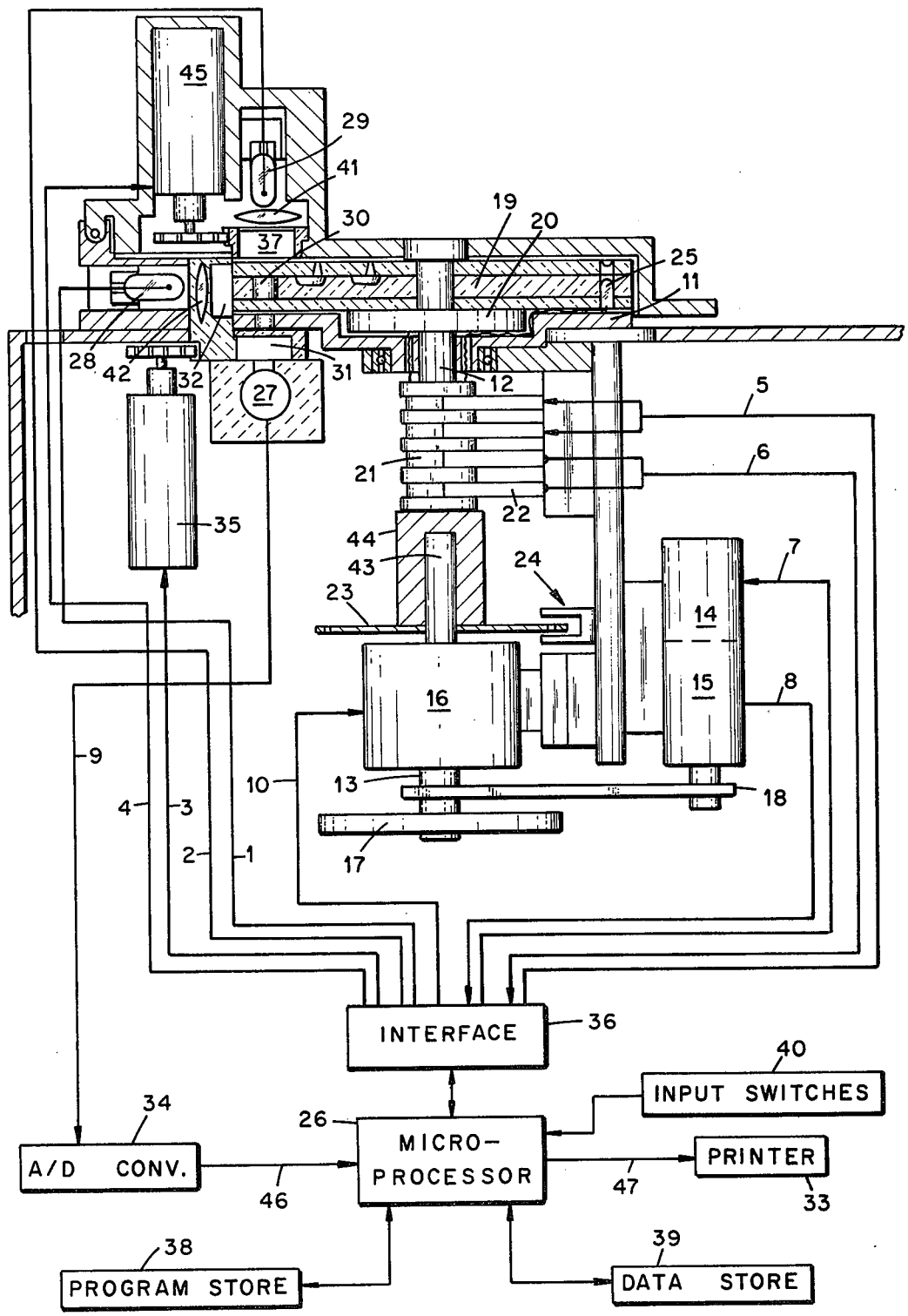
FIG. 1 is a schematic drawing of the fast photometer analyzer of the present invention for accomplishing the above objects.

In the analyzer system illustrated in FIG. 1 of the drawings, a motor 14 is connected to an idler shaft 13 by means of a belt device 18. A tachometer generator 15 is attached to the motor 14 for the purpose of generating a voltage proportional to the speed of the motor. A flywheel 17 is attached to the shaft 13. A clutch/brake 16 is connected between the idler shaft 13 and a rotor driving shaft 12 of the analyzer by means of a shaft 43 and a coupling member 44.

The other analyzer parts shown in FIG. 1 are of a more conventional nature. These include an encoding disc 23, which provides the timing for the rotor and cuvete pulses, and the associated photodetector (light source and detector) 24. It should be understood that two photodetectors are generally employed in fast analyzers, but only one is shown here for simplicity. There are four slip rings 21 with their mating brushes 22, and the slip rings 21 are coupled to the rotor driving shaft 12. Two slip ring/brush combinations are used to carry the rotor temperature signal from a thermistor 25, and two are used to carry current to a thermoelectric heat pump module 20. The heat pump 20 is located in a recess in the rotor holder 11, and is positioned below a rotor 19 for any desired heating thereof. The thermistor 25 is encased in a copper-tipped pin that fits into a mating hole in the rotor 19 for monitoring the temperature of the rotor.

The system of lamps, lenses and filters is likewise of conventional design. A side lamp 28 is used for light scattering and fluorescence measurements and a lens 42 and a filter 32 are associated therewith. A top lamp 29 is used for transmission/absorbence measurements, and a lens 41 and filters 37 and 31 are associated therewith. A photomultiplier tube 27 receives the primary data signals from the solution(s) in the cuvete(s) in the rotor 19 and gives the signal values by means of a line 9 to a microprocessor 26 after passage through an A/D converter 34 and a lead connection 46. It should be understood that there are a plurality of filters 37, one of which is selected by the filter select motor 45, and also there are a plurality of filters 32 and 31, a pair of which is selected by the filter select motor 35 for any given mode of operation.

An interface 36 performs the necessary signal conversions between the fast analyzer and the microprocessor 26. The various signals include signals to the lamps 28 and 29 over leads 1 and 2 respectively; signals to the filter select motors 35 and 45 by means of leads 3 and 4, respectively; signals to the clutch/brake unit 16 by means of leads 10; signals to the heat pump 20 by means of the leads 5 and the associated pairs of brushes 22 and slip rings 21; signals from the thermistor 25 by means of the associated pairs of slip rings 21 and brushes 22, and leads 6 to the interface 36; signals to the motor 14 by means of the leads 7; and signals from the tachometer generator 15 by means of the leads 8 to the interface 36.

The microprocessor 26 is also interconnected to a program storage unit 38, to a data storage unit 39, to a printer 33 over a lead line 47, and to operator-actuated parameter input switches 40.

In the operation of the system of FIG. 1, the following input parameters are selected by the operator dialing a selected program into the microprocessor by means of the parameter input switches 40:

1. Initial motor speed (prior to acceleration of the rotor);
2. Running motor speed (during data acquisition);
3. Clutch/brake operating sequence;
4. Rotor temperature;
5. Filter selection (37 and/or 31, 32);
6. Photomultiplier tube high voltage; and
7. Lamp selection (29 and/or 28).

The rotor 19 is loaded into the analyzer and, while being rotated at about 50 rpm, is preheated or precooled to the desired temperature. Once the rotor is at the desired temperature (as determined by the thermistor 25) the following sequence of events occur under the control of the microprocessor:

1. The rotor is stopped with the light source 29 just in front of the first cuvete 30.
2. The motor 14 and the coupled flywheel 17 are accelerated to a speed of about 4500 rpm while at the same time the shaft 12 is held stationary by the energized brake of the unit 16, the appropriate lamp (29 and/or 28) is turned on, the filter combination is selected by the motor 45 and/or the motor 35, and the high voltage on the photomultiplier 27 is set.
3. The brake is deenergized and the clutch is energized in the unit 16. The rotor 19 is then accelerated to full running speed (about 4000 rpm) in about 100 msec.
4. Data acquisition begins at the beginning of the second revolution of the rotor, which is about 30 msec after the solutions have been transferred out into the cuvetes 30. This acquisition is usually revolutions-based and continues for the sampling interval and number of samples based on the numer of revolutions of the rotor. Each sample taken (transmission counts for each of the seventeen cuvetes) has a corresponding sample time that must be recorded to allow statistical interpretation of that data due to the changing rotor speed during the data acquisition.
5. The data is printed out on the printer 33.

Figure 2:
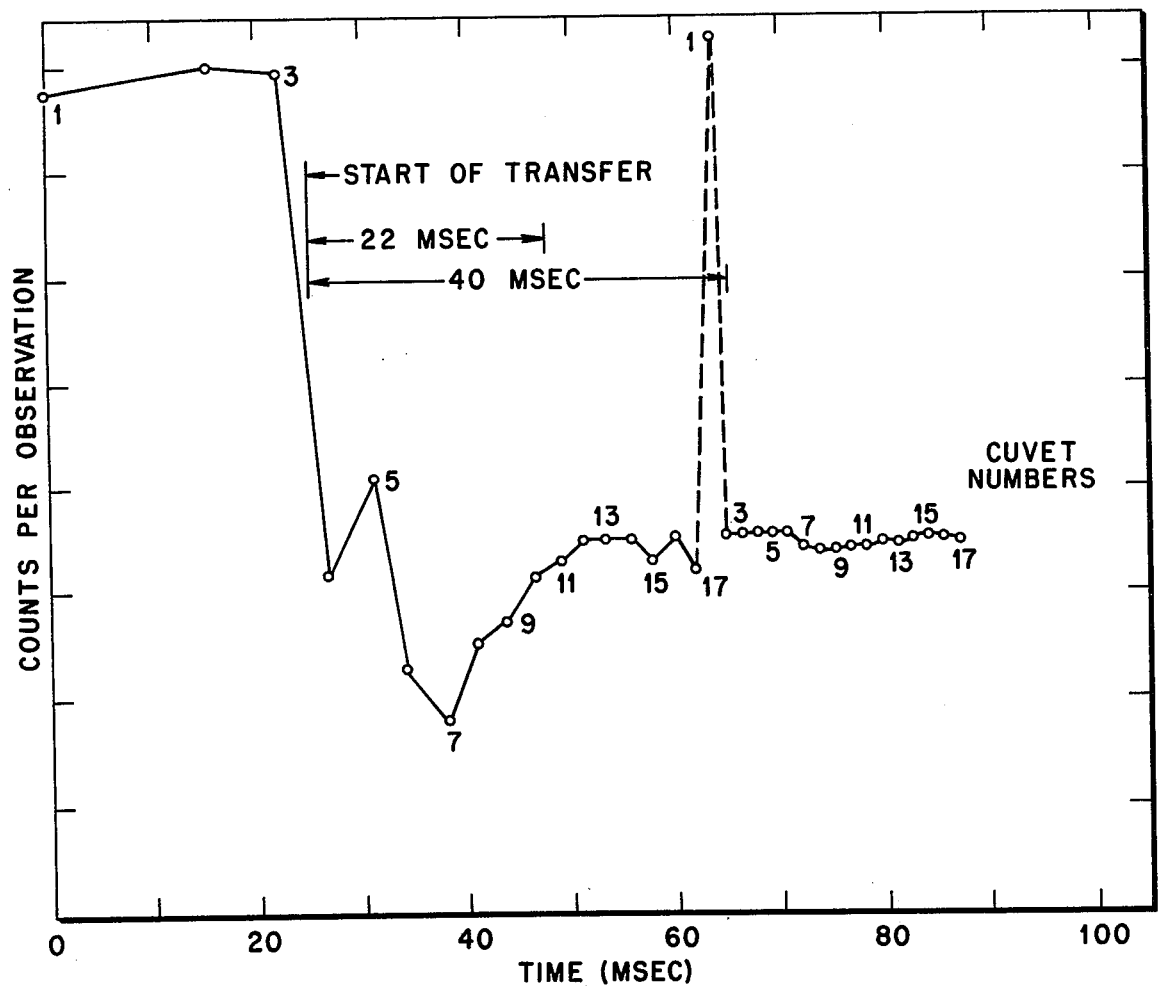
FIG. 2 is a graph of the counts per observation versus elapsed time for a mixture of two dye solutions utilizing the device of FIG. 1.

Turning now to the results, the graph shown in FIG. 2 is a plot of the counts per observation versus elapsed time for a mixture of two dye solutions at a constant acceleration of 3100 rad/sec$_2$. It will be seen that transfer is completed in a 40 msec period of revolution from cuvete 4 to cuvete 17, approximately. More than 90% of the absorbence is observed by cuvete 11 and the time interval to reach this cuvete is about 22 msec. Thus, transfer occurs completely in 22 to 40 msec after the liquid starts into the cuvetes. The rapid mixing of the respective samples and reagents in the respective cuvetes of the rotor, by the fast acceleration of the rotor after the clutch of the unit 16 is energized, will effect the rapid clearing away of any bubbles or froth from the reactions that would interfere with data taking.

The above results show that the system described above is therefore capable of remarkable fast time-based data acquisition, and is ideally suited to reaction rate and stopped-flow types of measurements.

It should be understood that there are at least three basic types of operation of the system of FIG. 1. The first is when only the lamp 29 is energized and the appropriate filter 37 is selected by the motor 45 for use with the lamp 29 for transmission/absorbence measurements; the second is when only the lamp 28 is energized and the appropriate pair of filters 31 and 32 are selected by the motor 35 for use with the lamp 28 for light scattering and fluorescence measurements; and the third is when neither lamp 28 nor 29 energized and chemiluninescence measurements from the reactions in the cuvetes are being made. It should be understood that there is still a fourth possible type of operation of the system of FIG. 1, if such is desired, wherein both the lamps 28 and 29 are alternately energized and the selected ones of the respective filters 31, 32 and 37 are selected for use with the respective lamps 28 and 29.

It should be apparent that this invention will allow rapid kinetic and stopped-flow analysis to be performed simultaneously up to 17 samples in parallel.

This invention has been described by way of illustration rather than by limitation and it should be apparent that it is equally applicable in fields other than those described.

What is claimed is:

1. In a minature fast photometer analyzer including a rotor holder, a driving shaft coupled to said holder, a removable rotor provided with a plurality of cuvetes positioned close to the outer edge of said rotor and adapted to receive respective samples and reagents thereinto upon acceleration of said rotor, said rotor adapted to be fixedly positioned onto said rotor holder, a photomultiplier, a filter, and a light source, the cuvetes of said rotor adapted to be sequentially passed between said light source and filter and said photomultiplier upon rotation of said rotor holder and rotor by said driving shaft, a printer, means for transmitting and processing the output signals of said photomultiplier and conveying them to said printer, said output signals being a function of the transmission/absorbence signals received throught respective ones of said rotor cuvetes containing said respective samples and reagents therein, a thermistor mounted in said rotor for monitoring the temperature thereof, a first pair of slip rings coupled to said drive shaft and electrically coupled to said thermistor, a first pair of brushes associated with and contacting said first pair of slip rings for conveying an output signal from said thermistor, and means for energizing said lamp and providing a high voltage to said photomultiplier, the improvement comprising a clutch/brake unit provided with an idler shaft and being coupled to said rotor holder drive shaft, said idler shaft having a flywheel affixed thereto, a drive motor provided with an output shaft, drive belt coupled to said motor output shaft and to said idler shaft, means for energizing said drive motor and means for selectively energizing the brake or clutch of said clutch/brake unit, whereby said brake is adapted to be energized with said clutch deenergized until a desired speed is reached by said drive motor and then said brake is adapted to be deenergized while said clutch is then energized and said rotor holder and affixed rotor are then brought up to a desired running speed in a rapid manner to effect the rapid mixing of said respective samples and reagents within said respective cuvetes thus minimizing the presence of any bubbles and froth therein such that the rapid acquisition of said output signals can be effected.

2. The analyzer set forth in claim 1, wherein said rotor holder is provided with a recessed portion, a heat pump mounted within said recessed portion, said heat pump adapted for use as a heating means for said rotor, a second pair of slip rings coupled to said drive shaft and electrically coupled to said heat pump, a second pair of brushes associated with and contacting said second pair of slip rings, and means connected to said second pair of brushes for selectively energizing said heat pump as a function of a desired rotor temperature as sensed by said thermistor.

3. The analyzer set forth in claim 2, wherein said desired motor running speed is about 4000 rpm.

4. The analyzer set forth in claim 3, wherein said rapid mixing of said respective samples and reagents within said respective cuvetes is effected in about 100 msec.

* * * * *